United States Patent [19]

Kaplan

[11] 4,052,513

[45] Oct. 4, 1977

[54] STABLE TOPICAL ANESTHETIC COMPOSITIONS

[75] Inventor: Carl Kaplan, Memphis, Tenn.

[73] Assignee: Plough, Inc., Memphis, Tenn.

[21] Appl. No.: 673,175

[22] Filed: Apr. 2, 1976

Related U.S. Application Data

[63] Continuation-in-part of Ser. No. 532,533, Dec. 13, 1974, abandoned.

[30] Foreign Application Priority Data

Dec. 11, 1975 United Kingdom ............... 50867/75

[51] Int. Cl.$^2$ .......................................... A61K 31/245
[52] U.S. Cl. ..................................... 424/310; 424/313
[58] Field of Search .......................... 424/310, 174, 60

[56] References Cited

U.S. PATENT DOCUMENTS

| | | | |
|---|---|---|---|
| 1,888,601 | 11/1932 | Mack et al. | 424/310 X |
| 1,907,392 | 5/1933 | Stover | 424/310 |
| 2,340,776 | 2/1944 | Stambovsky | 424/310 X |
| 2,382,546 | 8/1945 | Curtis | 424/310 X |
| 2,457,188 | 12/1948 | Stone | 424/310 |
| 3,322,624 | 5/1967 | Stone | 424/310 X |
| 3,479,428 | 11/1969 | Bryce et al. | 424/310 |
| 3,751,562 | 8/1973 | Nichols | 424/310 |
| 3,821,363 | 6/1974 | Black et al. | 424/60 X |

OTHER PUBLICATIONS

De Navarre, International Encyclopedia of Cosmetic Material Trade Names, 1957, pp. 323 and 11.

*Primary Examiner*—Dale R. Ore
*Attorney, Agent, or Firm*—Vincent H. Gifford; Stephen B. Coan; Bruce M. Eisen

[57] ABSTRACT

A cosmetically elegant and stable oil in water emulsion for use as a topical anesthetic containing 0.5–15% benzocaine solubilized in water with a dialkyl ester of an alkanedioic acid having the formula ROOC—$C_nH_{2n}$—COOR' where R and R' are alkyl groups of from 1 to 4 carbon atoms and $n$ is an integer from 1 to 8.

10 Claims, No Drawings

STABLE TOPICAL ANESTHETIC COMPOSITIONS

This is a continuation-in-part of Ser. No. 532,533 filed on Dec. 13, 1974, now abandoned.

BACKGROUND OF THE INVENTION

This invention relates to a stable cosmetically elegant lotion, cream or foam oil in water emulsion useful as a topical anesthetic which exhibits no microscopic crystallization. The preparation is designed for relief of surface pain and itching and provides soothing temporary relief of minor burns, cuts, scratches, sunburn and other minor skin irritations.

The most common pain relieving agent used in topical anesthetic compositions is benzocaine. Since benzocaine is only very slightly soluble in water, solvents other than water have generally been used in benzocaine preparations, such as the polyethylene glycol esters taught in U.S. Pat. No. 3,322,624. Attempts to solubilize benzocaine in water using various surfaceactive agents have been made. However, the resulting preparations were generally found to be unstable with the benzocaine crystallizing or settling out, the problem being particularly acute at benzocaine concentrations over 0.5%.

DETAILED DESCRIPTION OF THE INVENTION

Accordingly, it has now been found that a stable cosmetically elegant topical anesthetic formulation containing 0.5 to 15 percent of benzocaine can be prepared by incorporating 5 to 40 percent of a cosmetically acceptable dialkyl ester of an alkanedioic acid which is a liquid at 10° C and has the formula ROOC—$C_nH_{2n}$—COOR', where R and R' are alkyl groups of from 1 to 4 carbon atoms and $n$ is an integer from 1 to 8. Although the precise mechanism of action is not known, the esters will be referred to as solubilizers for the benzocaine. At least 5 percent benzocaine is preferred with the most preferred range of benzocaine in solution being 5 to 10 percent, which can generally be obtained by incorporating 15 to 30 percent of the solubilizer. All percentages mentioned throughout are by weight unless otherwise specified.

Either straight chained or branch chained alkyl groups can be used for the —$C_nH_{2n}$— chain, but the straight chained are preferred. The most preferred ester solubilizers are diisopropyl adipate and diethyl sebacate. Other contemplated ester solubilizers include dimethyl malonate, diethyl succinate, diethyl glutarate, diethyl adipate, dipropyl adipate, dibutyl sebacate, diisopropyl sebacate, diethyl pimelate, diethyl suberate, diethyl azelate, dibutyl adipate, dibutyl sebacate, methyl ethyl succinate, diethyl ethyl-isopropylmalonate, and diethyl isosuccinate. The solubilizers can be used either singly or in combination with one another. These solubilizers generally have the additional advantage of imparting desirable emollient properties to the inventive composition.

One or more cosmetically acceptable emulsifying agents are also necessary for the formulation. The particular emulsifer(s) used is selected on the basis of skin and chemical compatibility, cost, type of emulsion desired as well as the shelf life stability required. Surfactants of the nonionic type are preferred as the emulsifying agent in the formulation. Anionic emulsifiers are undesirable since they generally provide an alkaline environment in which benzocaine is less soluble. Cationic emulsifiers generally provide the desired acid environment but are generally found to be skin irritants and are accordingly cosmetically less desirable than the preferred nonionic sufactants. The number of suitable nonionic surfactants is legion; the most frequently used are:

a. esters of a polyethylene glycol having a molecular weight between about 200 and 600 particularly with fatty acids having 12 to 18 carbon atoms.

b. esters of sorbitol with fatty acids having 12 to 18 carbon atoms, e.g. Sorbitan Stearate, and the polyethenoxy ethers of said esters, e.g. Polysorbate-60.

c. polyethenoxy ethers of alkanes and alkyl phosphates having 12 to 18 carbon atoms, e.g. Coceth-6; PEG-75-Lanolin.

Concentrations of the nonionic surfactants would generally be in the range of 5 to 20 percent according to the solubilizer used and the benzocaine concentration desired.

Various optional ingredients may be included in the formulation such as perfumes; preservatives, e.g. parabens; antiseptics; pigments; humectant, e.g. PEG-8, propylene glycol; emollients, e.g. cetyl alcohol, lanolin; antioxidants; chelating agents, e.g. disodium EDTA; emulsion stabilizers, e.g. xanthan gum; dyes; propellants, e.g. propellant-12; foaming agents; viscosity control agents, e.g. paraffin; as well as any other class of material whose presence may be cosmetically or otherwise desirable.

The remainder of the composition would consist essentially of water which would generally be in the range of 30–90 percent, with a preferred range of 40–70 percent. It is, of course, understood that water is the external phase of an oil in water emulsion.

The following nonlimiting examples are presented to further illustrate a foam, cream and lotion form of the invention. The terminology used is in conformance with the CTFA Cosmetic Ingredients Dictionary. Although for convience the examples illustrate only diisopropyl adipate and diethyl adipate as the solubilizer, other dialkyl alkanedioates as described above could similarly be used to solubilize the benzocaine.

EXAMPLE I

A topical anesthetic lotion is prepared according to the following formulation:

| Part A: | Weight (Kg) |
| --- | --- |
| Diisopropyl Adipate | 15.0 |
| Benzocaine | 5.0 |
| Coceth-6 | 5.5 |
| Sorbitan Stearate | 5.0 |
| Polysorbate-60 | 4.0 |
| Propylparaben | 0.1 |
| Part B: | |
| Methylparaben | 0.2 |
| PEG-8 | 3.0 |
| Xanthan Gum | 0.1 |
| Disodium EDTA | 0.2 |
| Water | 61.9 |
| | 100.0 Kg |

The ingredients of Part A (oil phase) are heated and agitated at 80° C until the solids are melted. The ingredients of Part B (water phase) are heated and agitated at 80° C until the solids dissolve. The mixture of Part A is then slowly added to the mixture of Part B while agitating. The entire batch is cooled to 30° C and agitated until uniformity results.

EXAMPLE II

The following cream formulation is prepared in a manner similar to Example I:

| Part A: | Weight (Kg) |
|---|---|
| Diisopropyl Adipate | 15.0 |
| Benzocaine | 5.0 |
| Coceth-6 | 13.5 |
| Cetyl Alcohol | 1.0 |
| Paraffin | 1.0 |
| Lanolin | 2.0 |
| Part B: | |
| Methylparaben | 0.2 |
| PEG-8 | 3.0 |
| Xanthan Gum | 0.3 |
| Disodium EDTA | 0.1 |
| PEG-75 Lanolin | 3.0 |
| Water | 55.9 |
| | 100.0 Kg |

EXAMPLE III

The following foam formulation concentrate is prepared in a manner similar to Example I:

| Part A: | Weight (Kg) |
|---|---|
| Diisopropyl Adipate | 17.0 |
| Benzocaine | 5.0 |
| Coceth-6 | 3.0 |
| Polysorbate-60 | 2.5 |
| Sorbitan Stearate | 1.0 |
| Propylparaben | 0.1 |
| Part B: | |
| Methylparaben | 0.2 |
| Propylene Glycol | 3.0 |
| Disodium EDTA | 0.1 |
| Water | 68.1 |
| | 100.0 Kg |

The final foam formulation contains 90% concentrate and 10% of a suitable propellant, such as propellant-12.

EXAMPLE IV

A topical anesthetic lotion is prepared in a manner similar to Example I:

| Part A: | Weight (Kg) |
|---|---|
| Diethyl Adipate | 20.0 |
| Benzocaine | 10.0 |
| Coceth-6 | 5.5 |
| Sorbitan Stearate | 5.0 |
| Polysorbate-60 | 4.0 |
| Propylparaben | 0.1 |
| Part B: | |
| Methylparaben | 0.2 |
| PEG-8 | 3.0 |
| Xanthan Gum | 0.1 |
| Disodium EDTA | 0.2 |
| Water | 51.9 |
| | 100.0 Kg |

Numerous other variants of the above formulations will be apparent to one skilled in the art and within the spirit of the invention. What is claimed is:

1. A stable cosmetically elegant oil in water emulsion useful as a topical anesthetic comprising 0.5 to 15 percent of benzocaine; 5 to 40 percent of a cosmetically acceptable dialkyl ester of an alkanedioic acid which is a liquid at 10° C and having the formula ROOC—$C_nH_{2n}$—COOR', where R and R' are alkyl groups of from 1 to 4 carbon atoms and $n$ is an integer from 1 to 8; at least one cosmetically acceptable surfactant, and water.

2. A composition according to claim 1 wherein $C_nH_{2n}$ is a straight chained alkyl group.

3. A composition according to claim 2 wherein said ester is diethyl sebacate.

4. A composition according to claim 2 wherein said ester is diisopropyl adipate.

5. A composition according to claim 4 wherein the benzocaine concentration is from about 5 to 10 percent and the diisopropyl adipate concentration is from about 15 to 30 percent.

6. A composition according to claim 1 wherein the benzocaine concentration is at least 5 percent.

7. A composition according to claim 1 wherein said surfactant comprises a nonionic surfactant.

8. A composition according to claim 7 wherein the concentration of said nonionic surfactant is in the range of 5 to 20 percent.

9. A composition according to claim 8 wherein the concentration of said water is in the range of 30 to 90 percent.

10. A method of alleviating minor pain of irritated skin comprising the step of applying the composition of claim 1 to the irritated skin.

* * * * *